US009368321B1

(12) United States Patent
Randolph et al.

(10) Patent No.: US 9,368,321 B1
(45) Date of Patent: Jun. 14, 2016

(54) FIDUCIAL-BASED CORRELATIVE MICROSCOPY

(71) Applicant: FEI Company, Hillsboro, OR (US)

(72) Inventors: Steven Randolph, Portland, OR (US); James Miyasaki, Aloha, OR (US); Marcus Straw, Portland, OR (US)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 14/579,056

(22) Filed: Dec. 22, 2014

(51) Int. Cl.
*H01J 37/22* (2006.01)
*G01N 21/64* (2006.01)
*H01J 37/26* (2006.01)

(52) U.S. Cl.
CPC .......... *H01J 37/222* (2013.01); *G01N 21/6428* (2013.01); *G01N 21/6486* (2013.01); *H01J 37/26* (2013.01); *G01N 2021/6439* (2013.01); *H01J 2237/26* (2013.01)

(58) Field of Classification Search
USPC .......................... 250/304, 307, 306, 309, 310
See application file for complete search history.

(56) References Cited

U.S. PATENT DOCUMENTS

| 8,422,777 B2* | 4/2013 | Aller | ..................... | G06K 9/3216 |
| | | | | 382/165 |
| 2014/0072095 A1* | 3/2014 | Feser | ................. | G01N 23/2206 |
| | | | | 378/4 |

OTHER PUBLICATIONS

Shtengel, Gleb, et al., "Interferometric fluorescent super-resolution microscopy resolves 3D cellular ultrastructure," PNAS, 2009, pp. 3125-3130, vol. 106, No. 9.

Watanabe, Shigeki, et al., "Protein localization in electron micrographs using fluorescence nanoscopy," NIH Public Access, Author Manuscript, 2011, pp. 1-16.
Kukulski, Wanda, et al., "Correlated fluorescence and 3D electron microscopy with high sensitivity and spatial precision," JCB: Article, 2011, pp. 111-119, vol. 192, No. 1.
Kopek, Benjamin, G., "Correlative 3D superresolution fluorescence and electron microscopy reveal the relationship of mitochondrial nucleoids to membranes," PNAS, 2012, pp. 6136-6141, vol. 109, No. 16.
Chakraborty, Anirban, et al., "Adaptive Geometric Tessellation for 3D Reconstruction of Anisotropically Developing Cells in Multilayer Tissues from Sparse Volumetric Microscopy Images," PLOS ONE, 2013, pp. 1-14, vol. 8, Issue 8.
Gibson, Eli, et al., "3D prostate histology image reconstruction: Quantifying the impact of tissue deformation and histology section location," J Pathol Inform, 2013, vol. 4, No. 31.
Huang, Jianyong, et al., "A Digital Volume Correlation Technique for 3-D Deformation Measurements of Soft Gels," International Journal of Applied Mechanics, 2011, pp. 335-354, vol. 3, No. 2.

* cited by examiner

*Primary Examiner* — Kiet T Nguyen
(74) *Attorney, Agent, or Firm* — Michael O. Scheinberg; Scheinberg & Associates

(57) ABSTRACT

A method is provided for preparing a sample for correlative optical and electron imaging and correcting aberrations in the imaging process due to sample deformation. Dye-coated fiducial markers are distributed throughout the sample volume. The fiducial markers are preferably in the form of polystyrene nanospheres that are functionalized on their surface and subsequently treated with a fluorescent dye. The dye does not penetrate the sphere but only binds to the surface. By limiting the dye to the surface of the nanospheres, the shape of the spheres can be determined in iPALM and in charged particle images aiding in tracking of physical changes that may occur to the sample volume.

19 Claims, 6 Drawing Sheets

FIDUCIAL-BASED CORRELATIVE MICROSCOPY

TECHNICAL FIELD OF THE INVENTION

The present invention relates to correlative microscopy and in particular to correlative light and electron microscopy imaging.

BACKGROUND OF THE INVENTION

Microscopic images of cellular structure in biological samples can reveal important information regarding biological processes and cellular architecture. A correlative approach, which uses both optical microscopy and electron microscopy, produces the most comprehensive results. For example, light microscopy information can be used to identify areas of biological importance and their dynamics within a sample. Then electron microscopy can be used to resolve structural details within those areas after fixation and/or staining.

Images collected with a conventional optical microscope are limited in resolution to about half of the wavelength of the light used. For practical optical microscopy this limit is around 200 nm. Because of this limitation, conventional optical microscopes are said to be diffraction limited. Many techniques exist for improving resolution beyond the diffraction limit. Such techniques are called super-resolution techniques. One particular technique is stochastic optical reconstruction microscopy (STORM). Another technique is photo-activated localization microscopy (PALM). These techniques are used to form an image of a sample using fluorescent markers which can be switched between an "on" state, in which the marker fluoresces, and an "off" state, in which the marker does not fluoresce. STORM typically uses fluorescent organic dyes whereas PALM typically uses fluorescent proteins. The switching between states is realized when the markers enter a dark state after fluorescent emission and are then insensitive to excitation for a period of time. Due to this inactivation, the vast majority of markers are in the dark state at a given time with only a small number emitting fluorescent light. In forming a super-resolution image of a sample, a large series of separate images of the sample are collected to localize each individual marker independent of neighboring markers.

In the separate images, each marker appears as a diffraction-limited point-spread function. A Gaussian fit is applied to each point-spread function, and the marker location is now represented by a point at the center of the Gaussian fit. By sequential imaging and application of this process to each marker, a super-resolution image of the sample is built up, allowing imaging past the diffraction limit. Different colored fluorescent dyes can be imaged simultaneously using, for example, dichroic optics selected to separate the emissions of different markers based on their emission spectra. Using several wavelength channels can allow imaging of several different cellular components simultaneously.

One variation of the PALM is interferometric PALM, or "iPALM." By arranging multiple lenses, for example one lens above and one lens below the sample, fluorescent light collected can be caused to interfere with itself so as to produce an interference pattern which depends on the difference in the optical path length between the two lens systems. This allows localization in the Z dimension.

Non-superresolution techniques such as confocal imaging also allow for three dimensional fluorescence imaging albeit with reduced resolution. The invention may also be advantageous to correlative microscopy involving these types of optical imaging modalities as well.

Correlative microscopy involves overlaying one or more images created with one imaging technique with one or more images created using another imaging technique. For example, one image may be formed by an optical microscope and another image may be formed by a charged particle beam microscope. In one example, iPALM is used to form an optical image and a scanning electron beam is used to form a series of images, and the images are correlated. The iPALM technique provides localization information about specific regions in a sample, while an image from the electron microscope can show overall characteristics of a sample. This process is especially useful in the imaging of biological samples in which specific proteins or other structures in the biological sample can be chemically functionalized with organic dyes or genetically modified to express fluorescent protein, which can be imaged with iPALM. Correlating iPALM data with data from a charged particle system provides contextual information about the location of the fluorescent marker within the ultrastructure of the sample. Choosing appropriate charged particle preparation and imaging techniques, a three dimensional image can be constructed to give an excellent perspective of where in a sample specific features are located.

In the correlative microscopy example described above, iPALM is used to obtain three-dimensional super-resolution fluorescent images of a sample, first by sequentially localizing an area of interest in an X-Y image plane and rendering a two-dimensional super-resolution image from the molecular coordinates. Simultaneous multiphase interference of light emitted from each molecule is further used to extract a Z axis location, defining a third dimension. The same samples imaged using iPALM are then imaged by a charged particle system. The charged particle system may operate in a cycle in which, for example, a focused ion beam (FIB) removes a few-nanometer-thick layer of sample to expose a new surface that is imaged by SEM. This cycle may repeat numerous times to form a stack of images of ever-deeper layers in the sample.

Correlation of iPALM and electron microscopy (EM) images, however, is limited. Existing methods for correlation involve the use of a planar layer of fiducials at the interface of the sample volume and a supporting substrate. This allows accurate location information in the X-Y plane, but poor localization in the Z-plane. For example, correlation in the two dimensional X-Y plane produces excellent data using the technique as described in U.S. Pat. No. 7,924,432, issued to Hess et al. ("Hess"). In this technique, correlation in the X and Y dimensions are generally straightforward. However, the correlation of the Z plane using the method of Hess relies on interpolation between the top and bottom surfaces of the sectioned sample. This becomes problematic because the sample section can undergo changes due to electron and ion beam-induced distortion as well as changes that can occur in the sample due to sample preparation and insertion into vacuum for charged particle processing.

When biological samples are prepared for charged particle microscopy, physical changes to the sample often result. These physical changes can occur due to the "wet" preparation of a sample. One example of such a preparation is staining the sample with heavy metal stains which are visible in a charged particle system. Physical changes can also result from exposure of a sample to the vacuum environment in the charged particle system. These physical changes degrade the ability to correlate iPALM images with charged particle images of the same sample to obtain valuable information of the sample especially in the Z dimension.

Some attempts have been made to overcome the deficiencies of accurate imaging in the Z dimension. Such attempts include the use of fluorescent markers on the top surface of the sample. However, such attempts do not overcome the deficiencies in data correlation due to deformation of the sample. Another difficulty presented by current methods of using fluorescent markers is the presence of fluorescent dye throughout the sample volume containing the markers. If dye is present throughout the sample volume, typically too much dye is present for accurate localization of the marker using the stochastic iPALM or STORM process, which requires imaging individual single photon emission events. As a result, the brightness of a dye dispersed throughout the sample volume may produce so much fluorescence that it is difficult to accurately locate nearby areas of interest.

SUMMARY OF THE INVENTION

The invention comprises a method for accurate correlation in three dimensions of optical images and charged particle images.

Some embodiments provide a method of distributing objects or fiducials throughout a sample volume. These fiducials are visible in both optical and charged particle images, and can be used to correlate locations within the sample in images from optical methods with those from charged particle imaging. In some embodiments, the shape of the fiducial as well as the location of fiducial is used to correlate the images.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which.

DETAILED DESCRIPTION OF THE PREFERRED EMBODIMENTS

Figure 1:
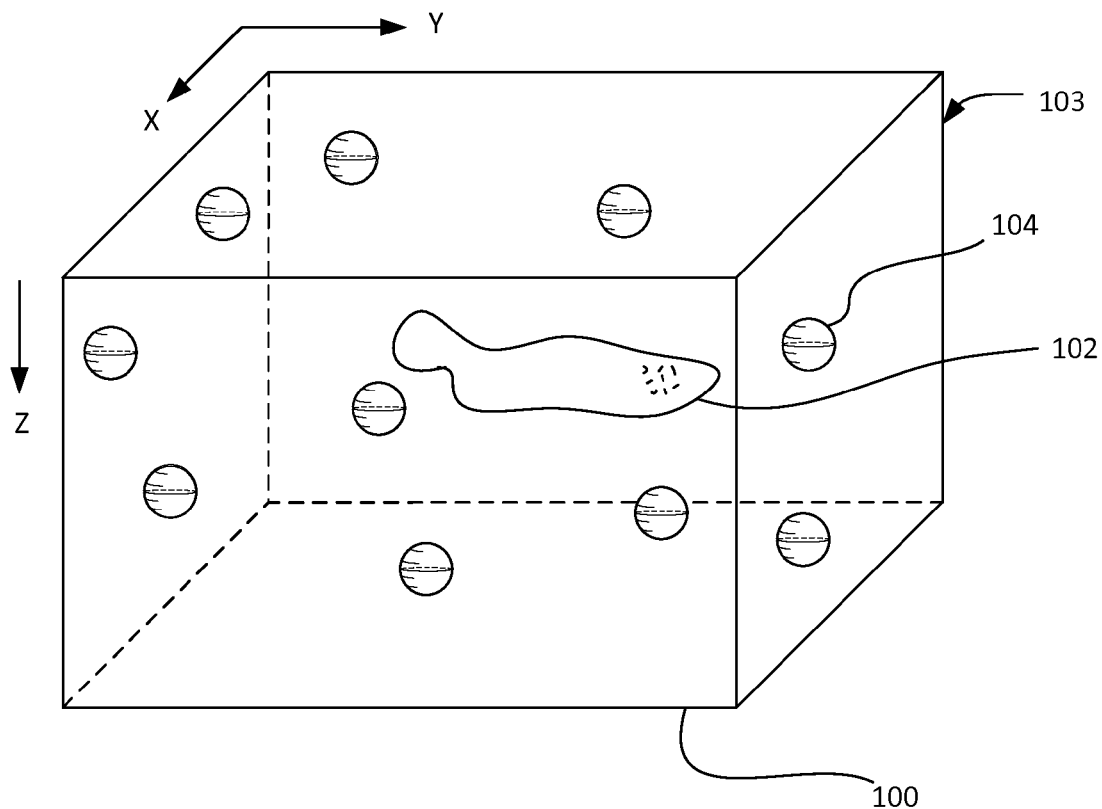
FIG. 1 shows a sample with multiple fiducials embedded throughout the sample volume.

The methods described herein produce three-dimensional images of a sample with more accurate correlation data between optical microscopy and electron microscopy. The methods are not limited to any particular optical microscopy technique or to any particular charged particle beam imaging technique. The invention can be used with diffraction limited optical techniques and super-resolution optical techniques. Embodiments can also be used with both broad field optical techniques, such as PALM, iPALM, STORM, SIM, STED, structured illumination techniques, and 4Pi, as well as scanning techniques, such as scanning confocal microscopy, near field scanning optical microscopy, and TIRF. The invention can be used with deterministic super-resolution techniques, such as STED, GSD, RESOLFT and SSIM, as well as stochastic super-resolution techniques, such as SOFI and all single-molecule localization methods (SMLM) such as SPDM, SPDMphymod, PALM, FPALM, STORM and dSTORM. These techniques are listed as example, and not as limitations on the application of the invention.

Charged particle imaging techniques that can be used in embodiments of the invention include scanning electron microscopy, scanning ion microscopy, transmission electron microscopy, and scanning transmission electron microscopy, including variations of those techniques, such as transmission electron microscopy tomographic techniques.

Some embodiments of the invention include the use of nanospheres having markers on their surfaces. In some embodiments, the surfaces can be functionalized and subsequently treated to provide markers, such as fluorescent dyes. Such treatment of the nanospheres preferably limits the presence of dye to the surface. By limiting the dye to the surface of the nanospheres, the shape of the spheres can be more easily determined in optical images aiding in tracking of physical changes that may occur to the sample volume.

Once three-dimensional images of a sample volume have been obtained using super-resolution microscopy and charged particle microscopy, the locations and shape of the fiducials contained in the sample volume can be compared, and a correction made to align the locations. This allows superior correlation between locations in a super-resolution image and a charged particle image, especially in the Z-axis.

Imaging in the X-Y dimensions, as well as initial imaging in the Z dimension, can be carried out using known systems and methods. One such method is shown and described in U.S. Pat. No. 7,924,432, for "Three-Dimensional Interferometric Microscopy, issued to Hess et al, which is hereby incorporated by reference. In the method described in Hess, two-dimensional correlation in the X-Y dimensions are carried out using a gold nanorod technique and correlation in the Z dimension is performed based on interpolation between top and bottom surfaces of the imaged section. In one embodiment, applicants prepare the sample by interspersing the sample volume with multiple fiducial markers that have been coated with a dye. Embedding the sample with the dye-coated fiducials enables super-resolution localization of the fiducials relative to objects of interest in the sample. Comparison of the shape of a single fiducial between imaging processes is possible as well. Additionally, dye-coated fiducials within the sample allow for accurate location relative to other dye-coated fiducials. This method can be used to correct correlative imaging rather than relying on the current method of interpolation between top and bottom surfaces of the sample.

Figure 2:
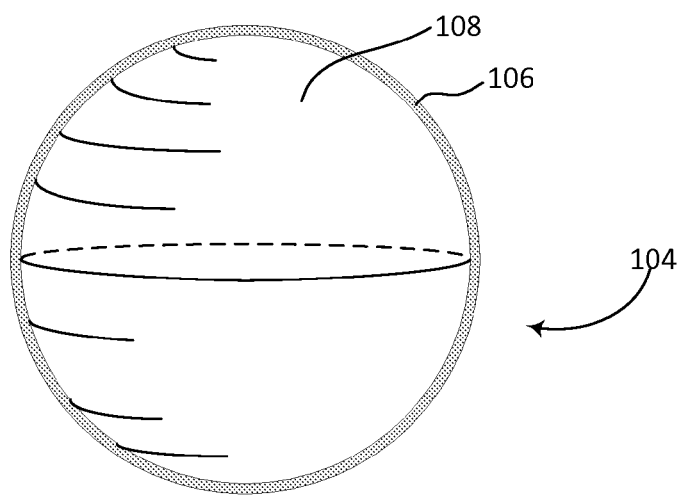
FIG. 2 shows a dye-coated spherical fiducial according to an embodiment of the invention.

FIG. 1 shows a sample 100 having an area of interest 102, such as a biological cell, embedded within a fixative material 103, such as resin. Sample 100 includes multiple fiducial markers preferably in the shape of spheres 104 embedded within sample 100 and distributed throughout the sample volume. As seen in FIG. 2, each marker is preferably a sphere 104, such as commercially available polystyrene or latex spheres, although various shapes and materials are contemplated by this invention. Other types of fiducials could be used, such as functionalized silica beads, particles with fluorescent coatings, quantum dots, nanoparticles, nanorods, chemically functionalized nano or microstructures.

Each sphere has affixed markers that can be observed in the optical microscope. For example, fluorescent makers, quantum dots, metal nanoparticles, or other markers can be used. Any method of affixing the markers to the sphere can be used. In one embodiment, the spheres are polystyrene and each sphere 104 undergoes chemical treatment to affix functional groups to the surface of the sphere, for example, amine (R—$NH_2$) groups may be introduced on the surface. These amino terminations may then be reacted with a sulfodichlorophenol ester derivative of, for example, an AlexaFluor 488 dye, available from Life Technologies, Grand Island, N.Y. This dye coating 106 is applied only to the outer surface of each sphere 104 so that the interior volume 108 of each sphere remains undyed and transparent in the imaging process. It should be noted that other types of functional groups and dyes may be used to coat the markers and that the markers may be of a shape and configuration other than spherical provided they can be reliably imaged via light and charged particle microscopy. For example, chemically functionalized carbon nanotubes or nanofibers linked to fluorescent dye may be used. The spheres 104 are then dispersed in, for example, an agarose solution within which, for example, a biological cell is present. The sample is then dehydrated and infiltrated with acrylic resins resulting in permanent embedding of the biological cells along with the dye-coated spheres 104. Other combinations of chemical functional groups on the sphere surface, dye derivatives, or lack thereof, are also possible methods of introducing dye to a nanosphere.

Figure 3:
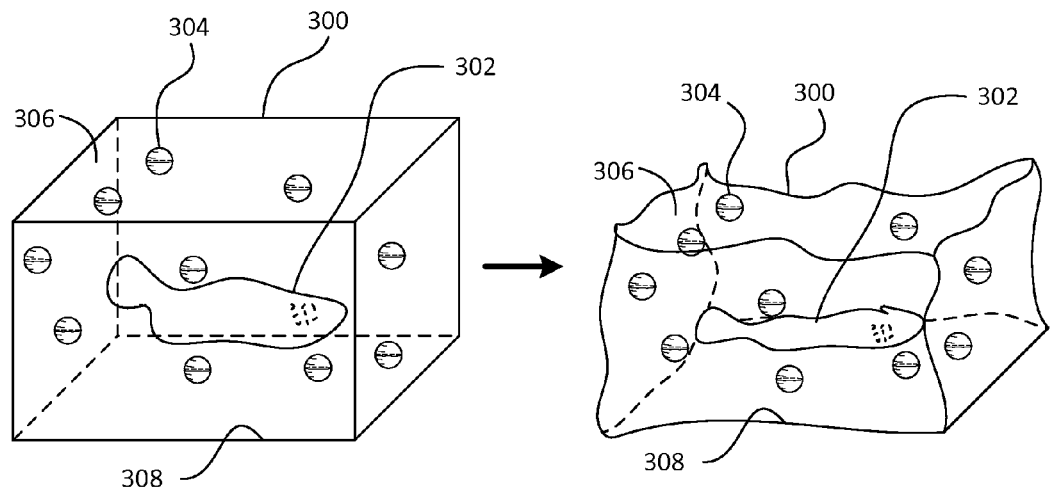
FIG. 3 is a view of a sample before and after undergoing physical deformation.

FIG. 3 shows a sample volume before and after undergoing physical changes. Physical changes to sample 300 may be a result of post-iPALM sample preparation, beam exposure during serial sectioning, exposure to a vacuum environment, or other causes. Sample 300 is seen on the left side of FIG. 3 prior to undergoing any physical deformation containing an embedded area of interest, such as, biological cell material 302 and multiple spheres 304 dispersed throughout the sample volume. Prior to undergoing any physical changes it can be seen that sample 300 is essentially symmetrical with outer surfaces that are substantially parallel. For example, upper surface 306 is substantially parallel with lower surface 308. As seen on the right side of FIG. 3, sample 300 is shown after physical deformation in which a number of changes to sample 300 occur. More specifically, upper and lower surfaces 306 and 308 are no longer substantially parallel. Additionally, the relative locations of cell material 302 and spheres 304 have changed as a result of the change in shape of the sample volume. In addition to locational changes, spheres 304 may themselves undergo a physical change in which they are no longer in the initial spherical shape. Since each sphere 304 is provided with a layer of dye molecules only on the outer surface the sphere as best seen in FIG. 2, sparse labeling is obtained so that the fluorescence of one sphere does not interfere with nearby spheres. Therefore, accurate locations of individual spheres and/or other objects of interest, such as specific protein molecules within the sample, are obtained. Additionally, the dye-coat on the outer surface of the sphere allows for optical imaging through the sphere so that it appears transparent and hollow in an image. The centroid of the sphere or other shape can then be located. The centroid used as a reference point for determining relative spacing between fiducials and other objects in the sample volume. Furthermore, the deviation of the sphere from its optimal spherical shape as well as its location relative to other spheres can be used to correct an imaged section obtained using charged particle microscopy. This correction allows improved accuracy of correlation between iPALM and electron images.

Figure 4:
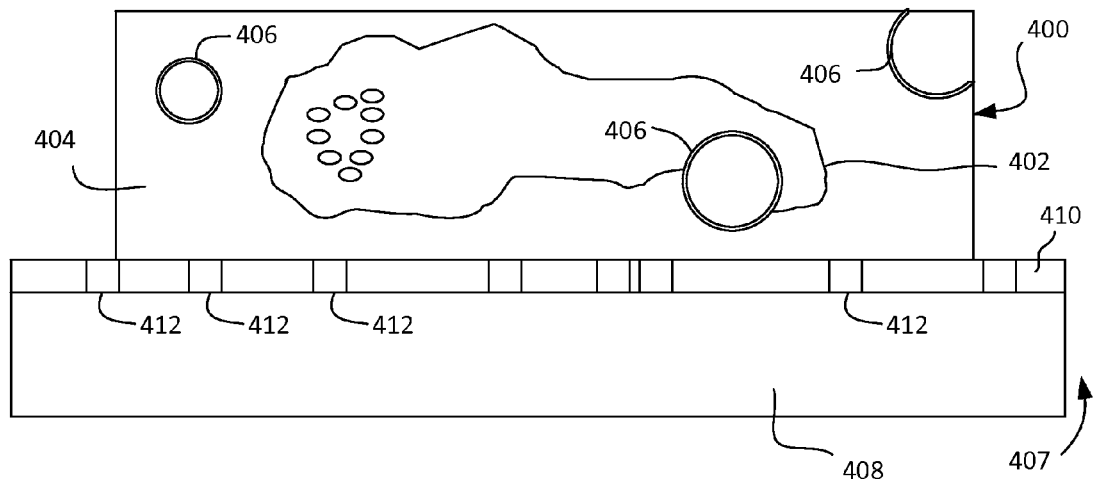
FIG. 4 shows a sample according to the invention mounted onto a substrate for imaging.

FIG. 4 shows a sample 400 having a cell structure 402 or other area of interest embedded within a resin 404 or other fixative material. Multiple dye-coated spheres 406 are dispersed within the resin 404 for use as three-dimensional fiducial markers for correlating iPALM data with FIB-SEM slice-and-view data. Dye-coated spheres 406 are easy to locate in both iPALM and electron imaging. Sample 400 is mounted on a support 407 of a glass coverslip 408 with an ITO coating 410 containing gold nanorods 412. Initial calibration in the Z dimension using the gold nanorods is conducted as shown and described in U.S. Pat. No. 7,924,432, issued to Hess et al. However, the dispersion of the dye-coated spheres 406 allows for direct correlation between iPALM data and EM data throughout the entire volume of the sample.

Figure 5:
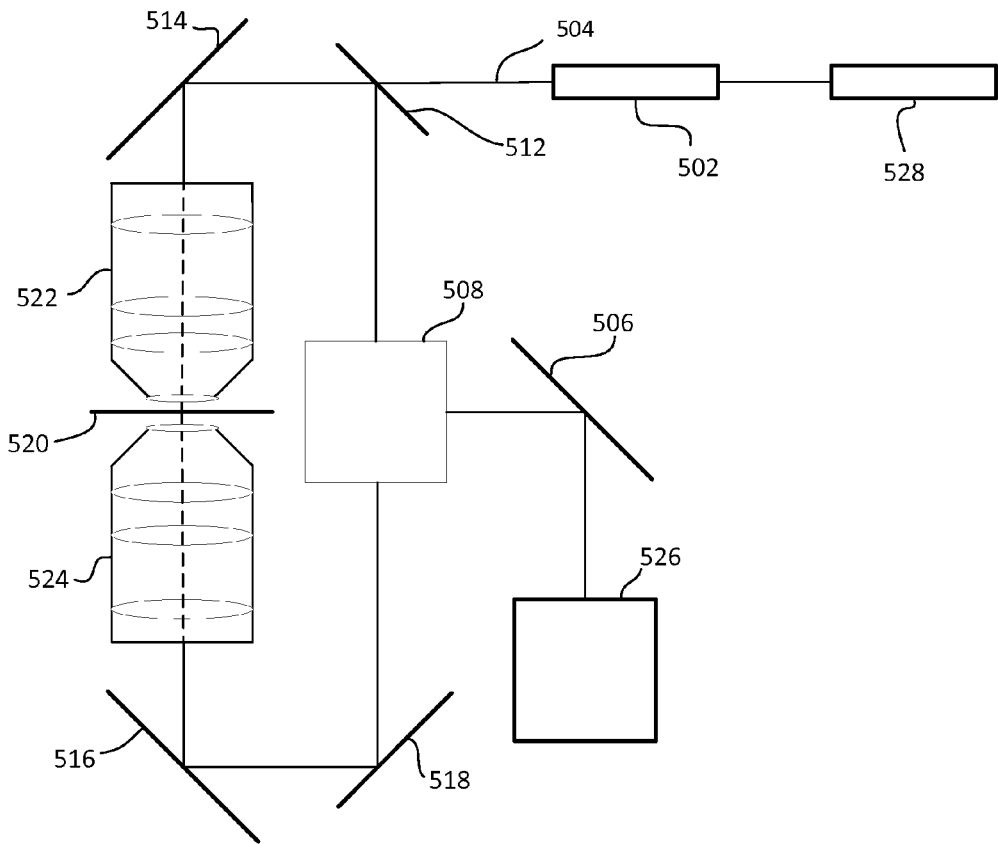
FIG. 5 shows a schematic view of an optical microscope for illuminating and view fluorescent fiducial markers.

Embodiments of the invention can be implemented in existing systems that include an optical microscope for illuminating and viewing fluorescent markers and a dual beam system that may include an ion beam column and electron beam column. FIG. 5 shows a super-resolution optical system 500. The system has an excitation source 502 emitting an excitation beam. The beam may be combined with a depletion source 528 emitting a depletion beam. The combined beam 504 reflects off mirror 514, and is focused into a small spot in the sample volume 520. Other embodiments may feature different optical beam paths without deviating from the scope of the invention. Photons emitted by de-excited molecules in the sample volume are collected by lenses 522 and 524, and recombined in prism 508. An interference pattern results from this recombination and is collected by collector 526. Analysis of the interference pattern allows the production of accurate three-dimensional images of a sample volume.

Figure 6:
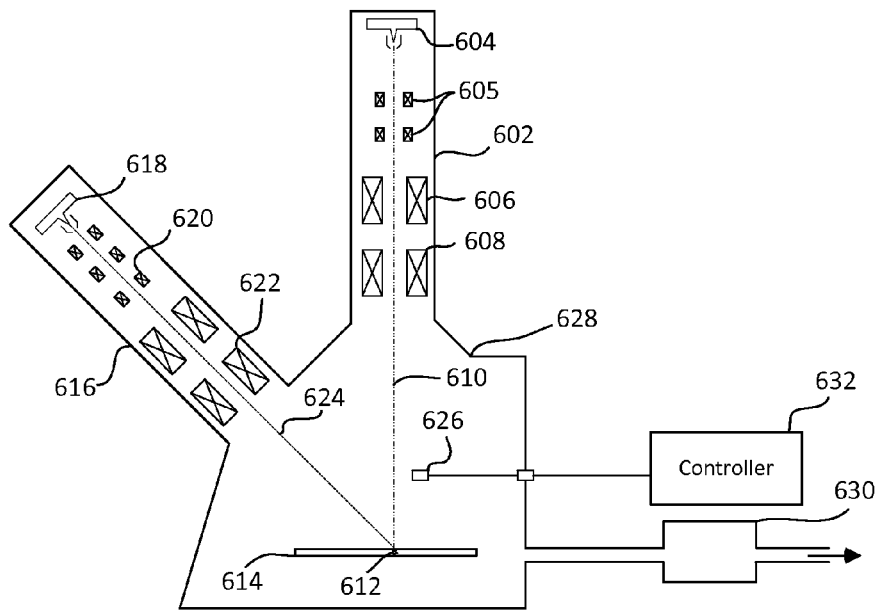
FIG. 6 shows a schematic view of a dual beam system including an electron beam column and an ion beam column.
Figure 7:
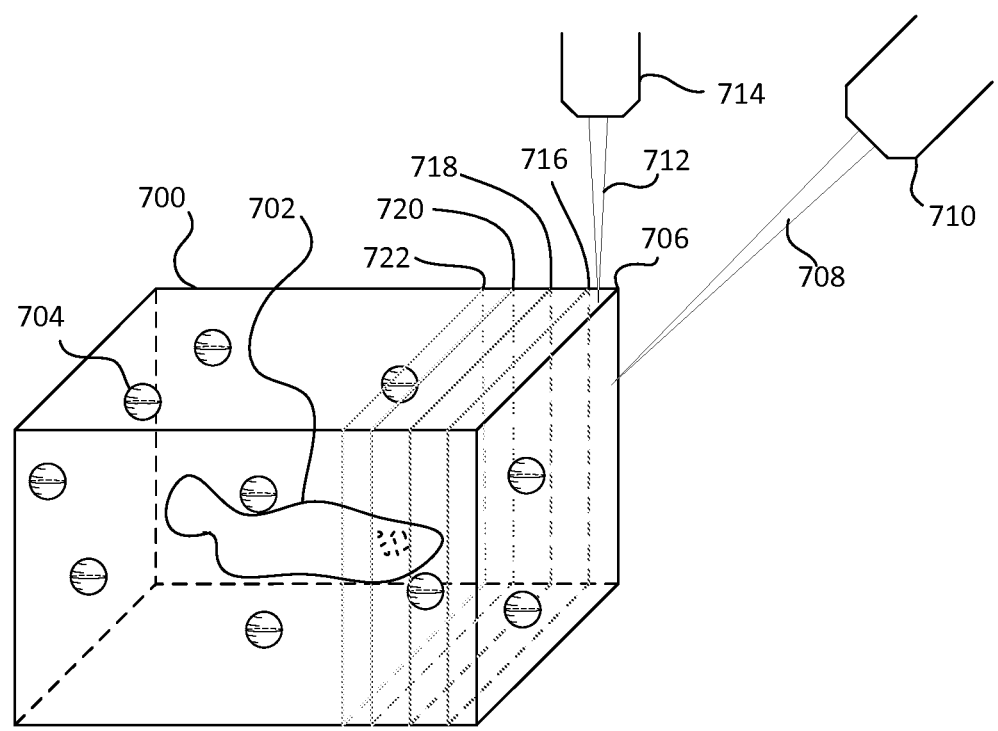
FIG. 7 shows a slice and view process for a sample using the dual beam system.

A typical dual charged particle beam system 600 is shown in FIG. 6. System 600 includes an electron beam column 602 with an electron source 604, deflectors 605, electron optical lenses 606 and 608, which focus and direct an electron beam 610 towards a sample 612 mounted on sample stage 614. System 600 also includes a focused ion beam column 616 with an ion source 618, ion optical lenses 620 and 622, which focus and direct an ion beam 624 towards sample 612. Electron and ion beam columns 602 and 618 and a particle detector 626 are contained within a vacuum chamber 628, which is evacuated by vacuum pump 630. A controller 632 controls both electron and ion columns 602 and 618 as well as detector 626. FIG. 7 shows a slice and view process performed by the dual beam system 600 on sample volume 700 with an embedded structure 702 and distributed dye-coated spheres 704. Sample face 706 is imaged by electron beam 708 from electron beam column 710. After imaging, a planar layer of the sample volume is removed by milling with focused ion beam 712 from focused ion beam column 714. Milling this layer exposes a new sample face 716, which is then imaged with electron beam 708. This process then repeats with focused ion beam 712 milling and exposing new sample face 718 which is then imaged. The process continues with more layers to expose new sample faces 720 and 722 which are imaged and removed. The size and number of layers is variable depending on the size and location of the area of interest. Ion beam systems are also capable of producing images in a similar process to electron imaging. Ion microscopy could be used in place of electron microscopy. In addition, other methods are known to create three dimensional charged particle images, such as electron tomography or methods collecting depth information based on the charged particle beam energy.

Figure 8:
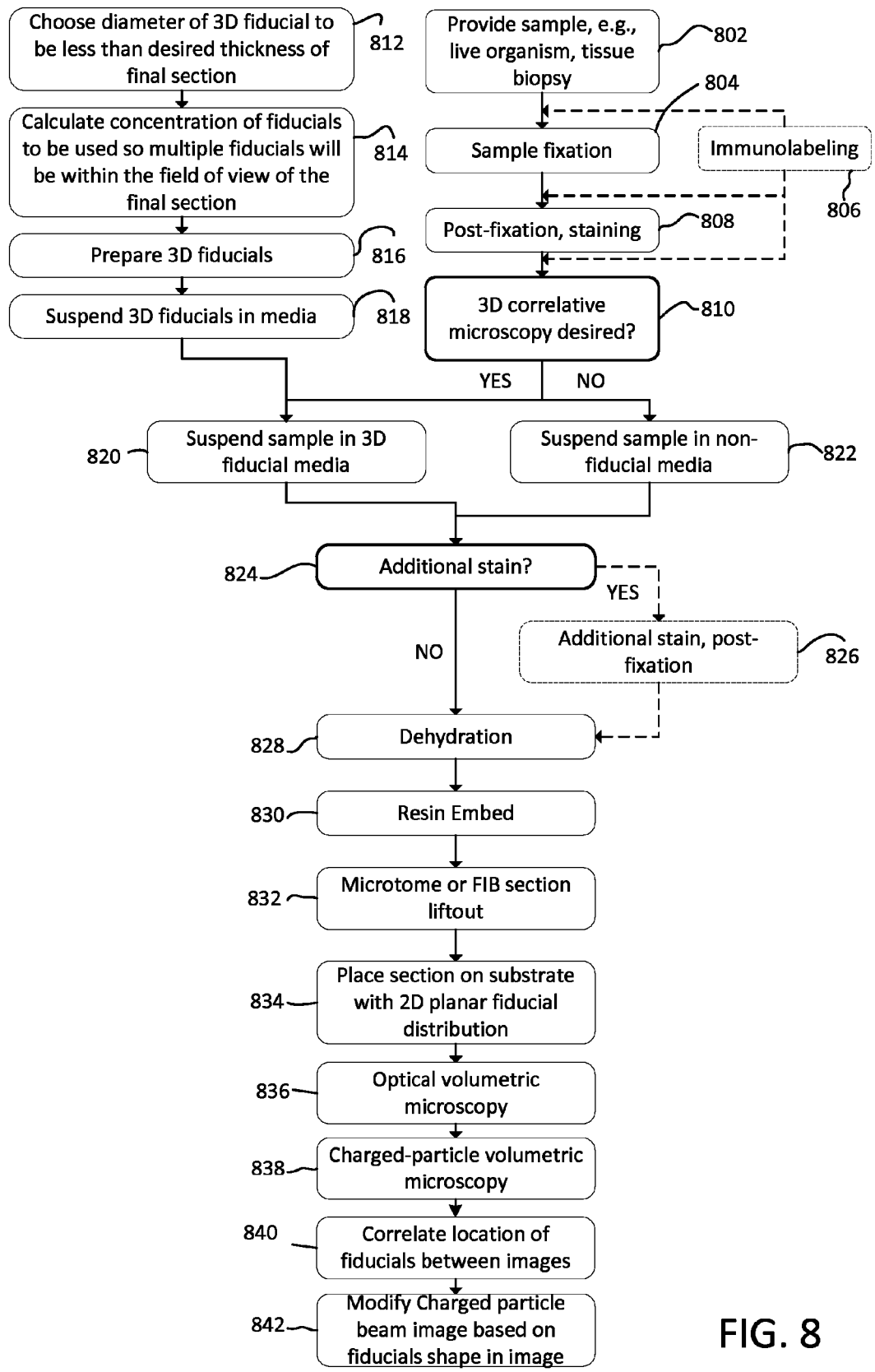
FIG. 8 is a flow chart showing the steps for preparing a sample for correlative light and electron microscopy.

FIG. 8 shows a method of preparing a sample for correlative light and electron microscopy and the correlative imaging process. The process begins with a sample 802 which can be a live organism, a tissue biopsy, or other types of samples. While much of this specification is directed towards biological samples, other types of samples may be examined using this method as well. The sample is fixed 804 and stained 808 using methods well known in the art. Immunolabeling 806 may be used at any point in the sample preparation process and allows localized staining of specific areas in the sample with fluorescent or heavy-metal markers. Separate from initial sample preparation, 3D fiducials are prepared. In step 812, the size of fiducials is chosen so as to have a diameter less than the desired thickness of the final sample section. In step 814, the concentration of fiducials required is calculated, so that multiple fiducials will be present within the field of view of the final sample section, but not so many fiducials are present as to make visualization of the component parts of the sample difficult.

In an embodiment of the invention, the fiducials are polystyrene spheres. The spheres may be chemically modified on the surface to allow bonding of a dye, for example by chemical binding of aliphatic amine or other functional groups to the surface of the sphere. Chemical modification of the sphere surface allows bonding of a fluorescent dye to only the surface of the sphere without dye penetration into the interior of the sphere. When a sphere is sliced and imaged, it appears as a ring if the interior has been exposed as a result of the slicing. Locating the dye only on the surface of the fiducial is advantageous as it allows more precise location information about the fiducial, as well as information about deformation of the sphere during subsequent sample processes. The fiducial's susceptibility to heavy metal stains may be advantageous as well. For example, osmium tetroxide may selectively stain unsaturated hydrocarbons in the sphere, resulting in improved SEM contrast.

In step 818, the fiducials are suspended in a media, and are ready for introduction of the sample. The media is often a viscous solution, for example, an agarose gel. Step 810 is a decision of whether correlative microscopy is desired. As described earlier, correlative microscopy has many desirable features. If correlative microscopy is not desired, the sample continues to suspension in a media which does not contain fiducials. If correlative microscopy is desired, the sample is suspended 820 in the fiducial-containing media prepared earlier. A decision is made in step 824 whether or not to apply an additional staining step 826 to the sample. In an embodiment, additional staining involves the use of heavy metal stains, such as osmium tetroxide or uranyl acetate. Following additional staining, if implemented, the sample is dehydrated 828. This may be performed using various methods, which are well known in the art. For example, the water content of the sample may be replaced progressively with a miscible solvent, such as ethanol.

After dehydration, the sample can be embedded 830 in a plastic resin, and prepared for thin sectioning. Sectioning 832 of the sample may be performed by, for example, ultramicrotomy, or sectioning using a focused ion beam. Thin sections of the sample are then placed on a substrate in step 834. In some embodiments, the substrate takes the form of a planar substrate with fiducials distributed across the surface, forming a two-dimensional array of fiducial markers at the boundary of the sample volume and the substrate. In some embodiments, the fiducials are gold nanorods and the substrate is a glass coverslip as shown in FIG. 4. Once the sample has been applied to the substrate, it is ready for imaging. Generally, an optical imaging step 836 is preferred as the first imaging process, as the optical imaging process typically does not cause noticeable physical changes in the sample volume. Charged particle imaging in step 838 is then performed.

Figure 9:
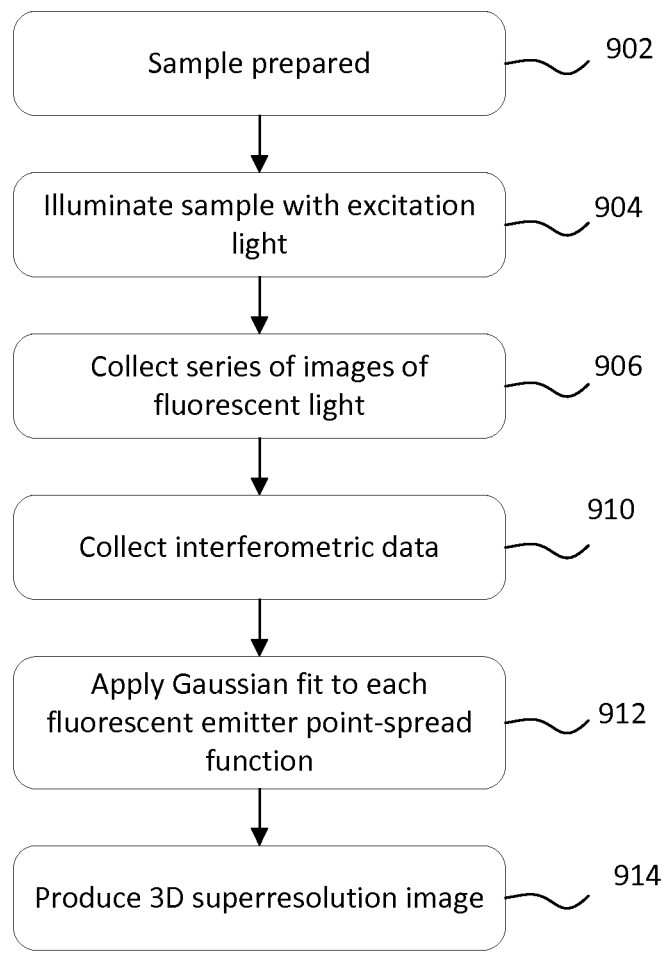
FIG. 9 is a flow chart showing the steps for iPALM.

In some embodiments, 3D super-resolution images are produced using interferometric PALM, as shown in FIG. 9. A prepared sample 902 is placed in a microscope, such as the one shown in FIG. 5, and illuminated with excitation light in step 904. A series of fluorescent images 906 are then obtained. At the same time, interferometric data is collected 908 as well, which can be interpreted to provide Z-axis information. A Gaussian fit is then applied 910 to each emitter point-spread function, and is combined with the interferometric Z-axis data to give a point in three dimensions. These points make up the final 3D image 912. In some embodiments, multiple fluorescent markers are imaged consecutively. Markers are chosen to have non-overlapping fluorescence emission spectra, so their fluorescence can be separated through the use of, for example, dichroic optics.

Upon introduction of the sample into the vacuum chamber of the charged particle microscope, physical changes can occur to the sample volume, as seen most clearly in FIG. 3. For example, the sample may shrink or deform, resulting in loss of correlation between locations in the sample volume between the two microscopic techniques used. This invention improves correlation between optical and charged particle images of a sample volume. Fiducial markers, prepared and distributed as described earlier are visible in both optical super-resolution images as well as charged particle images. The distribution and location of fiducial markers throughout the sample volume can therefore be determined in both optical and charged particle volumetric images. Because the fiducial markers are immobile within the sample volume matrix, they move along with any physical changes that the sample volume undergoes, along with features of interest within the sample volume. Through accurate three dimensional location of the fiducial markers within the sample volume in both optical and charged particle imaging, the amount of movement of each fiducial between imaging techniques can be determined, and therefore the amount of deformation of the sample volume between imaging processes. In addition, any change of shape of the fiducials can be used for determination of deformation of the sample volume. Correction can then be applied to either set of images to allow accurate correlation between imaging methods.

In step 840 (FIG. 8), the location of the fiducials in the optical image are correlated to the location of the fiducials in the charged particle beam image. A useful correlation technique is presented by Huang et al, *Int. Journal of Applied Mechanics* 03, 335 (2011) "Huang". Huang uses a set of digital volume correlation algorithms to address three-dimensional deformation measurements of soft gels using laser-scanning confocal microscopy. A first algorithm is used to accelerate the integer-voxel correlation computations. Then, two different algorithms are used to obtain sub-voxel displacement and strain fields of volume images before and after deformation. Although Huang correlates images of different layers of a sample from laser-scanning confocal microscopy, the techniques used by Huang may be used to correlate optical and EM images. Peeters et al, *Ann. Biomed. Engineering*, *October* 2004; 32(10):1443-1452 describes another possible method for quantification of the deformation between subsequent images, as does Unlu et al, *Medical Imaging*, Vol. 5747. Other methods may use edge detection in both charged particle and optical images, and apply a 3D transformation to the images to match the edges between optical and charged particle images.

The distorted image in the electron microscope can be "undistorted" by redistributing the pixels in the series of images so that the fiducials in the EM images match the locations in three dimensions of the location of the fiducials in the optical image. Moreover, in step 842 distortion can also be determine by deviations of the electron beam image of the fiducials from the original spherical shape, and the pixels of the EM image can be rearranged so that the images of the fiducials show the fiducials are spheres. A preferred method or apparatus of the present invention has many novel aspects, and because the invention can be embodied in different methods or apparatuses for different purposes, not every aspect need be present in every embodiment. Moreover, many of the aspects of the described embodiments may be separately patentable. The invention has broad applicability and can provide many benefits as described and shown in the examples above. The embodiments will vary greatly depending upon the specific application, and not every embodiment will provide all of the benefits and meet all of the objectives that are achievable by the invention.

It should be recognized that embodiments of the present invention can be implemented via computer hardware, a combination of both hardware and software, or by computer instructions stored in a non-transitory computer-readable memory. The methods can be implemented in computer programs using standard programming techniques—including a non-transitory computer-readable storage medium configured with a computer program, where the storage medium so configured causes a computer to operate in a specific and predefined manner—according to the methods and figures described in this Specification. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits programmed for that purpose.

Further, methodologies may be implemented in any type of computing platform, including but not limited to, personal computers, mini-computers, main-frames, workstations, networked or distributed computing environments, computer platforms separate, integral to, or in communication with charged particle tools or other imaging devices, and the like. Aspects of the present invention may be implemented in machine readable code stored on a non-transitory storage medium or device, whether removable or integral to the computing platform, such as a hard disc, optical read and/or write storage mediums, RAM, ROM, and the like, so that it is readable by a programmable computer, for configuring and operating the computer when the storage media or device is read by the computer to perform the procedures described herein. Moreover, machine-readable code, or portions thereof, may be transmitted over a wired or wireless network. The invention described herein includes these and other various types of non-transitory computer-readable storage media when such media contain instructions or programs for implementing the steps described above in conjunction with a microprocessor or other data processor. The invention also includes the computer itself when programmed according to the methods and techniques described herein.

Computer programs can be applied to input data to perform the functions described herein and thereby transform the input data to generate output data. The output information is applied to one or more output devices such as a display monitor. In preferred embodiments of the present invention, the transformed data represents physical and tangible objects, including producing a particular visual depiction of the physical and tangible objects on a display.

Although much of the previous description is directed at mineral samples from drill cuttings, the invention could be used to prepare samples of any suitable material. The terms "work piece," "sample," "substrate," and "specimen" are used interchangeably in this application unless otherwise indicated. Further, whenever the terms "automatic," "automated," or similar terms are used herein, those terms will be understood to include manual initiation of the automatic or automated process or step.

In the following discussion and in the claims, the terms "including" and "comprising" are used in an open-ended fashion, and thus should be interpreted to mean "including, but not limited to . . . . " To the extent that any term is not specially defined in this specification, the intent is that the term is to be given its plain and ordinary meaning. The accompanying drawings are intended to aid in understanding the present invention and, unless otherwise indicated, are not drawn to scale. Particle beam systems suitable for carrying out the present invention are commercially available, for example, from FEI Company, the assignee of the present application.

Although the present invention and its advantages have been described in detail, it should be understood that various changes, substitutions and alterations can be made to the embodiments described herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method for three-dimensional correlation of locations of regions of interest in a sample volume utilizing images acquired optically and with a charged particle beam system, comprising:
   providing a sample volume supported on a substrate, the sample volume containing regions of interest and including fiducials distributed throughout the sample volume identifiable in both optical and charged particle images of the sample volume;
   introducing the sample volume into an optical system;
   imaging the sample volume using the optical system;
   identifying the three-dimensional location of the fiducials distributed throughout the sample volume using one or more optical images;
   introducing the sample volume into a charged particle beam system;
   imaging the sample volume using a charged particle beam;

identifying the three-dimensional location of the fiducials distributed throughout the sample volume using one or more charged particle images; and correlating locations of regions of interest in the sample volume using the location of the fiducials in the optical and charged particle beam images.

2. The method of claim 1, wherein the fiducials distributed throughout the sample volume includes fluorescent markers.

3. The method of claim 2, wherein the fluorescent markers are distributed throughout the sample volume in a concentration that is sufficiently low to enable imaging of each fluorescent marker individually without substantial interference from nearby fluorescent markers.

4. The method of claim 1, further comprising a planar layer of fiducials in an X-Y plane at the interface of the sample volume and the substrate, said fiducials being distinguishable from those distributed throughout the sample volume.

5. The method of claim 1, wherein imaging the sample volume using an optical system comprises three-dimensional super-resolution imaging.

6. The method of claim 5, wherein super-resolution imaging comprises photo-activated localization microscopy.

7. The method of claim 1, wherein three-dimensional location of objects are obtained using the charged particle beam system by sequential imaging and material removal cycles.

8. The method of claim 7, wherein imaging comprises obtaining scanning electron microscope images and material removal comprises milling with a focused ion beam.

9. The method of claim 1, wherein the fiducials comprise fluorescent nanoparticles.

10. The method of claim 9, wherein the nanoparticles are dye-functionalized spheres.

11. The method of claim 10, wherein the dye-functionalized spheres contain dye that is present on the surface of the sphere and does not penetrate the interior of the sphere.

12. The method of claim 11 wherein the dye is a photoactivatable dye or protein.

13. The method of claim 9, wherein the nanoparticles are quantum dots.

14. A method for correction of spatial changes in a sample volume comprising:

providing a sample volume with fiducials dispersed throughout the sample volume;

imaging the sample volume using an optical system;

determining the three-dimensional location of the fiducials distributed throughout the sample volume using the optical image or images collected;

introducing the sample into a charged particle beam system;

imaging the sample using a charged particle beam;

determining the three-dimensional location of the fiducials distributed throughout the sample volume using the charged particle beam image or images collected;

comparing the location of the fiducials in the optical image or images with the location of the fiducials in the charged particle beam image or images;

calculating the difference in location of fiducials between the optical image or images and charged particle image or images, and;

applying a correction to the optical image or images or the charged particle image or images to account for spatial changes to the sample volume.

15. The method of claim 14, further comprising overlaying the optical image or images with the charged particle image or images after a correction has been applied.

16. The method of claim 14, wherein optical imaging comprises three-dimensional super-resolution imaging.

17. The method of claim 16, in which charged particle imaging comprises a series of images by sequential imaging and material removal cycles, the series of sequential images being able to be processed into a three-dimensional representation of the sample volume.

18. The method of claim 14, wherein the difference in location of fiducials is determined by comparing the relative distance between fiducials in the optical and charged particle image or images.

19. The method of claim 14, wherein any change in shape of the fiducials between optical imaging and charged particle imaging is calculated and used to apply a correction to the optical image or images or charged particle image or images.

* * * * *